United States Patent [19]

Dandiker et al.

[11] Patent Number: 5,425,950
[45] Date of Patent: Jun. 20, 1995

[54] CONTROLLED RELEASE PHARMACEUTICAL COMPOSITIONS

[75] Inventors: Yogendra Dandiker; Paul D. Huckle, both of Ware, Great Britain

[73] Assignee: Glaxo Group Limited, London, England

[21] Appl. No.: 250,948

[22] Filed: May 31, 1994

Related U.S. Application Data

[63] Continuation of Ser. No. 968,515, Oct. 29, 1992, abandoned.

[30] Foreign Application Priority Data

Oct. 30, 1991 [GB] United Kingdom ............... 9123026
Oct. 30, 1991 [GB] United Kingdom ............... 9123044
Feb. 18, 1992 [GB] United Kingdom ............... 9203364

[51] Int. Cl.⁶ .................. A61K 9/32; A61K 9/34; A61K 9/36
[52] U.S. Cl. .................. 424/480; 424/474; 424/475; 424/479; 424/481; 424/482
[58] Field of Search ............... 424/474, 475, 479, 480, 424/481, 482

[56] References Cited

U.S. PATENT DOCUMENTS

| | | | |
|---|---|---|---|
| 4,880,636 | 11/1989 | Franz | 424/480 |
| 4,892,741 | 1/1990 | Ohm et al. | 424/479 |
| 4,892,742 | 1/1990 | Shah | 424/480 |
| 4,966,772 | 10/1990 | Ohm et al. | 424/482 |

FOREIGN PATENT DOCUMENTS

| | | |
|---|---|---|
| 0384514 | 8/1990 | European Pat. Off. . |
| 2230185 | 10/1990 | United Kingdom . |
| 92/15295 | 9/1992 | WIPO . |

*Primary Examiner*—Thurman K. Page
*Assistant Examiner*—James M. Spear
*Attorney, Agent, or Firm*—Bacon & Thomas

[57] ABSTRACT

This invention relates to a controlled release pharmaceutical composition comprising: (a) an outer layer comprising a pH independent hydrophilic polymer together with one or more fillers; and (b) one or more inner layers each comprising an active ingredient; wherein the outer layer is gradually removed by a combination of dissolution and erosion following administration and the inner layer or layers is gradually removed by a combination of dissolution and erosion or disintegrates rapidly once exposed; and processes for the preparation thereof. In particular the invention relates to pharmaceutical compositions for the controlled release of $H_2$-antagonists or serotonin agonists or antagonists.

15 Claims, No Drawings

CONTROLLED RELEASE PHARMACEUTICAL COMPOSITIONS

This application is a continuation of application Ser. No. 07/968,515, filed Oct. 29, 1992, now abandoned.

The invention relates to pharmaceutical compositions for the controlled release of one or more active ingredients. In particular, the invention relates to pharmaceutical compositions for the controlled release of $H_2$-antagonists or serotonin agonists or antagonists.

Cimetidine, N-cyano-N'-methyl-N''-[2-[[(5-methyl-1H-imidazol-4-yl)methyl]thio]ethyl]guanidine, and its pharmaceutically acceptable salts are described in British Patent Specification No. 1397436. Delayed-release oral dosage forms of cimetidine and its pharmaceutically acceptable acid addition salts are described in European Patent Application No. 431877. Cimetidine is a histamine $H_2$-antagonist.

Ranitidine, N-[2-[[[5-(dimethylamino)methyl-2-furanyl]methyl]thio]ethyl]-N'-methyl-2-nitro-1,1-ethenediamine, and its pharmaceutically acceptable salts are described in British Patent Specification No. 1565966, and a particular crystalline form of ranitidine hydrochloride is described and claimed in GB-B-2084580. In both of these specifications there is reference to a variety of formulations including preparations for oral, topical, parenteral or rectal administration. Oral preparations of ranitidine are further described in GB-B-2142820, GB-B-2198352, GB-B-2218336, GB-B-2219940, GB-B-2222772 and GB-A-2229094.

Ranitidine is a potent histamine $H_2$-antagonist which, in the form of its hydrochloride salt, is widely used in the treatment of conditions where there is an advantage in lowering gastric acidity. Such conditions include duodenal and gastric ulceration, reflux oesophagitis and Zollinger-Ellison syndrome. Ranitidine may also be used prophylactically in surgical procedures, and in the treatment of allergic and inflammatory conditions where histamine is a known mediator.

The serotonin $S_2$-agonist sumatriptan, 3-[2-(dimethylamino)ethyl]-N-methyl-1H-indole-5-methanesulphonamide, is described in British Patent Specification No. 2162522 and is a compound having a combination of highly advantageous properties for the treatment of migraine. Sumatriptan is preferably administered in the form of its succinate.

The preparation of immediate release and sustained release dosage forms is well known. Recently dosage forms which provide for rapid release of an active ingredient after an initial time delay have been described. These latter have become known as pulsed release dosage forms. United Kingdom Patent Application No. 2230185A describes a tablet for oral administration which comprises two layers, one of which contains a drug for immediate release and the other contains a drug for sustained release. Thus the tablet essentially consists of two dosage forms bonded together. A problem with this type of tablet is that it is not simple to prepare efficiently using conventional tabletting machinery. European Patent Application No. 384514 relates to a "tablet-within-a-tablet" pharmaceutical composition which provides for a sustained dose of active ingredient followed by an immediate dose of active ingredient. Dosage forms for pulsed delivery are described, for example, in United Kingdom Patent Specification No. 2230441A. The described dosage form comprises a two-part capsule containing a water-swellable material to separate the capsule parts on swelling. Dosage forms of this type are relatively expensive and difficult to manufacture.

One major problem has been the provision of a pulsed release dosage form which uses conventional excipients and which can be prepared in a simple manner using conventional tabletting machinery. A further problem arises when aiming to prepare pulsed release dosage forms containing highly water-soluble active ingredients such as ranitidine. Some pulsed release devices rely on an outer layer comprised of a polymer which hydrates to form a gel matrix on coming into contact with gastro-intestinal fluid. European Patent Application No. 384514 describes such a device. In this device, once the outer layer has partially dissolved, leaving a loose gel network, gastrointestinal fluid wets the inner tablet. If the inner tablet contains a highly water-soluble active ingredient, this will leach out through the partially dissolved outer gel layer giving premature and unpredictable release and a non-distinct pulse, which in turn can lead to reduced absorption and insufficient plasma levels.

There is also a problem with preparing pulsed release dosage forms where relatively large doses of active ingredient are required, especially in the case of oral dosage forms. The cores of such dosage forms are necessarily large which in turn limits the thickness of the outer layer if the tablets are to remain easy to swallow. The problem is multiplied if the active ingredient is water-soluble since, if the outer layer is thin, the drug can leach out through the thin outer layer again giving unpredictable and premature release.

We have now found that, using conventional excipients and conventional tabletting machinery, it is possible to prepare dosage forms which allow for; for example:

i) pulsed release of an active ingredient; ii) immediate release of a first active ingredient followed by pulsed release of a second active ingredient; iii) delayed sustained release of an active ingredient; iv) sustained release of a first active ingredient and delayed sustained release of a second active ingredient; v) immediate release of a first active ingredient followed by sustained release of a second active ingredient, optionally followed by pulsed release of a further active ingredient.

The pharmaceutical compositions of the invention have the advantages associated with pulsed release, sustained release and/or delayed release dosage forms. Thus the pharmaceutical compositions of the invention allow for a reduction in the frequency of administration of an active ingredient, enhancing patient acceptability, and enable it to be released at a time when it would be inconvenient to the patient to administer medication, for example, when the patient is asleep, and also enable medication to be administered prior to the onset of symptoms. Further, when administered orally such dosage forms enable the site of drug delivery to be controlled and enable an optimal plasma concentration of active ingredient to be maintained. The dosage forms of the present invention allow the advantages of pulsed release, sustained release and/or delayed release dosage forms to be combined. In particular, the dosage forms of the invention allow quite complex dosage regimens to be implemented without the need for administration of many different dosage forms. This is particularly useful where the active ingredients are to be self-administered as it avoids reliance on the patient remembering to take a number of different dosage forms at varying intervals.

The pharmaceutical compositions of the invention are also able to provide a distinct pulse with no premature leakage of the active ingredient from the core, even when highly water-soluble active ingredients such as ranitidine are employed. The pharmaceutical compositions of the invention can readily be adapted to provide the specific "time-to-pulse" required. Batches of tablets having the same composition will have a predictable release profile with little batch-to-batch variation. The pharmaceutical compositions of the invention are able to provide reliable pulsed-release even when the thickness of the outer coating is limited, i.e. when large doses of active ingredient are required, and the active ingredient is highly water-soluble.

Thus, according to the present invention there is provided a pharmaceutical composition comprising:
(a) an outer layer comprising a pH independent hydrophilic polymer together with one or more fillers; and
(b) one or more inner layers each comprising an active ingredient;
wherein the outer layer is gradually removed by a combination of dissolution and erosion following administration and the inner layer or layers is gradually removed by a combination of dissolution and erosion or disintegrates rapidly once exposed.

In a preferred or alternative aspect the inner layer or layers disintegrate rapidly once exposed. Preferably, the pharmaceutical compositions of the invention have one or two or, more preferably, a single inner core layer comprising an active ingredient.

In a preferred or alternative aspect the pharmaceutical composition of the invention is additionally provided with a rapidly disintegrating outer coating, surrounding the pH independent hydrophilic polymer layer, comprising an active ingredient.

In a preferred or alternative aspect, when an additional rapidly disintegrating outer coating comprising an active ingredient is present or when the inner layer or layers is gradually removed by a combination of dissolution and erosion once exposed, the outer layer comprises a pH independent hydrophilic polymer together with one or more fillers and an active ingredient.

In a preferred or alternative aspect the outer layer comprises a pH independent hydrophilic polymer together with one or more fillers and substantially free of any active ingredient.

In a preferred or alternative aspect the pharmaceutical composition of the invention is additionally provided with an enteric coating surrounding the pH independent hydrophilic polymer layer.

The pharmaceutical compositions of the invention may be presented in any suitable dosage form, in particular in dosage forms suitable for oral, rectal or vaginal administration such as tablets, suppositories and pessaries.

Suitable active ingredients for use in the pharmaceutical compositions of the invention include, for example analgesics, anti-inflammatories, bronchodilators, such as salbutamol, hypnotics, hypotensives, steroids, anti-migraine compounds such as serotonin agonists, e.g. sumatriptan and $H_2$-antagonists.

Further suitable active ingredients include agents for treating lower gastrointestinal tract diseases such as irritable bowel syndrome for example the serotonin antagonist compounds described in EP-A-0501322 in particular [1-[2-[(methylsulphonyl)amino]ethyl]-4-piperidinyl]methyl 5-fluoro-2-methoxy-1H-indole-3-carboxylate and pharmaceutically acceptable salts and solvates thereof.

Yet further suitable active ingredients include the $5HT_3$ serotonin antagonists ondansetron and pharmaceutically acceptable salts and solvates thereof, e.g. the hydrochloride dihydrate, 2,3,4,5-tetrahydro-5-methyl-2-[(5-methyl-1H-imidazol-4-yl)methyl]-1H-pyrido[4,3-b]indol-1-one and pharmaceutically acceptable salts and solvates thereof, e.g. the hydrochloride salt, (+)-1,2,3,9-tetrahydro-9-methyl-3-[(5-methyl-1H-imidazol-4-yl)methyl]-4H-carbazol-4-one and pharmaceutically acceptable salts and solvates thereof, e.g. the hydrochloride salt, 6-fluoro 2,3,4,5-tetrahydro-5-methyl-2-[(5-methyl-1H-imidazol-4-yl)-methyl]-1H-pyrido[4,3b]indol-1-one, and pharmaceutically acceptable salts and solvates thereof.

The pharmaceutical compositions according to the invention may contain a $5HT_3$antagonist, e.g. ondansetron, in combination with one or more other antiemetic compounds such as dexamethasone.

Preferably, the pharmaceutical compositions of the invention comprise salbutamol or, more preferably, a serotonin agonist, e.g. sumatriptan, a serotonin antagonist, e.g. [1-[2-[(methylsulphonyl) amino]ethyl]-4-piperidinyl]methyl 5-fluoro-2-methoxy-1H-indole-3-carboxylate and pharmaceutically acceptable salts and solvates thereof, or an $H_2$-antagonist, such as sufotidine or ranitidine as active ingredient.

Thus, in a preferred or alternative aspect the invention provides a pharmaceutical composition comprising:
(a) an outer layer comprising a pH independent hydrophilic polymer together with one or more fillers;
(b) an inner core comprising an $H_2$-antagonist;
wherein the outer layer is gradually removed by a combination of dissolution and erosion following administration and the inner core disintegrates rapidly once exposed.

In a preferred or alternative aspect the $H_2$-antagonist-containing pharmaceutical compositions of the invention are additionally provided with a rapidly disintegrating outer coating, surrounding the pH independent hydrophilic polymer layer, comprising an $H_2$-antagonist to provide an immediate release of drug.

In a preferred aspect the $H_2$-antagonist is ranitidine, cimetidine, sufotidine, famotidine, roxatidine or nizatidine, preferably cimetidine or, more preferably, ranitidine. The term 'ranitidine' encompasses pharmaceutically acceptable salts thereof. Such salts include salts with inorganic acids, such as hydrochlorides, hydrobromides and sulphates, and organic acids, such as acetates, maleates, succinates, fumarates and ascorbates. A particularly preferred salt is the hydrochloride.

The $H_2$-antagonist-containing pharmaceutical compositions of the invention may be presented in any suitable dosage form, in particular in dosage forms suitable for oral administration such as tablets.

In a preferred or alternative aspect the invention also provides a pharmaceutical composition comprising:
(a) an outer layer comprising a pH independent hydrophilic polymer together with one or more fillers;
(b) an inner core comprising sumatriptan;
wherein the outer layer is gradually removed by a combination of dissolution and erosion following administration and the inner core disintegrates rapidly once exposed.

In a preferred or alternative aspect the sumatriptan-containing pharmaceutical compositions of the invention are additionally provided with a rapidly disintegrating outer coating, surrounding the pH independent hydrophilic polymer layer, comprising sumatriptan to provide an immediate release of drug.

The sumatriptan-containing pharmaceutical compositions of the invention may be presented in any suitable dosage form, in particular in dosage forms suitable for oral or rectal administration such as tablets and suppositories.

When in the compositions according to the invention, a layer or layers is "gradually" removed, this means that the layer is removed over a time period of, for example, 1–8 hours, such as 1–3.5 hours, 2–5 hours or 4–6 hours following administration.

When in the compositions according to the invention, a layer or layers disintegrates "rapidly", this means that the layer disintegrates over a time period of, for example, less than 30 minutes, for example less than 10 minutes once exposed.

It will be appreciated that the rapidly disintegrating inner layer or layers in the compositions according to the invention will only start to disintegrate once the outer pH independent hydrophilic polymer layer has been removed to expose a portion or all of the inner layer.

The term "pH independent hydrophilic polymer" will be well-understood by those skilled in the art. Such polymers dissolve/erode after administration at a rate which is independent of the pH of the surrounding fluid.

Such polymers include, for example, cellulose ethers, polyvinylpyrrolidone, mixtures of natural hydrophilic gums, e.g. guar gum, gum Karaya, tragacanth and xanthan gum, and mixtures thereof. Preferably cellulose ethers will be employed, most preferably hydroxypropylmethylcellulose.

Fillers for use in the tablets of the invention will be those fillers known to those skilled in the art.

Such fillers may be soluble or insoluble and swelling or non-swelling and include, for example microcrystalline cellulose, dibasic calcium phosphate, tribasic calcium phosphate, calcium carbonate, calcium sulphate, dextrose, kaolin, lactose, powdered cellulose, pregelatinised starch, starch, sucrose and mixtures thereof. Preferred fillers include microcrystalline cellulose and dibasic calcium phosphate.

Other excipients which may be used in the polymer layer include lubricants conventional to the art, such as magnesium stearate, zinc stearate, calcium stearate, stearic acid, sodium stearyl fumerate, hydrogenated vegetable oils, glyceryl palmitostearate, glyceryl behenate, sodium benzoate, sodium lauryl sulphate, magnesium lauryl sulphate, mineral oil, talc and mixtures thereof; glidants conventional to the art such as colloidal silicon dioxide; disintegrants conventional to the art, such as carboxymethylcellulose calcium, carboxymethylcellulose sodium, magnesium aluminium silicate, microcrystalline cellulose, polacrilin potassium, pregelatinized starch, sodium alginate, sodium starch glycolate, and mixtures thereof; surfactants conventional to the art, such as anionic (e.g. sodium lauryl sulphate), cationic or neutral surfactants; ionic salts conventional to the art (e.g. sodium chloride); and dyes and pigments conventionally used in the art of pharmacy.

A preferred lubricant for inclusion in the polymer layer is sodium stearyl fumerate.

A preferred glidant for inclusion in the polymer layer is colloidal silicon dioxide.

In a preferred aspect the outer polymer layer comprises a pH independent hydrophilic polymer (e.g. hydroxypropylmethylcellulose), one or more fillers (e.g. microcrystalline cellulose, dibasic calcium phosphate), a lubricant (e.g. sodium stearyl fumerate), and a glidant (e.g. colloidal silicon dioxide).

Preferably the outer layer will comprise from 20 to 85% w/w of a pH independent hydrophilic polymer, preferably hydroxypropylmethyl cellulose, e.g. 20 to 40% w/w.

The rapidly disintegrating inner layer or layers and the rapidly disintegrating outer coating may comprise, in addition to the active ingredient, excipients such as fillers, binders, disintegrants and lubricants. Suitable fillers, disintegrants and lubricants are those mentioned above. Suitable binders include methylcellulose, sodium carboxymethylcellulose, hydroxypropyl methylcellulose, alginic acid, ethylcellulose, acacia, gelatin, pregelatinized starch, sucrose syrup, polyvinylpyrrolidone and guar gum.

In a preferred aspect the rapidly disintegrating inner layer or layers and the rapidly disintegrating outer layer comprises, in addition to the active ingredient, one or more fillers (e.g. microcrystalline cellulose, lactose), binders (e.g. polyvinylpyrrolidone, pregelatinised starch), disintegrants (e.g. microcrystalline cellulose, pregelatinised starch) and lubricants (e.g. sodium stearyl fumerate, magnesium stearate).

The rapidly disintegrating inner layer or layers and the rapidly disintegrating outer coating may conveniently have the same composition.

When the pharmaceutical compositions of the invention (i.e. tablets) are provided with an enteric coating, this will delay the initiation of the erosion/disintegration of the underlying pH independent hydrophilic polymer layer until the tablet reaches a region of the gastrointestinal tract where a specific pH prevails.

Such enteric coated tablets allow targeting of drugs to the colon for either a direct local action, or to provide a preferred site for drug delivery.

Enteric coatings for use in the tablets of the invention will be those coatings known to those skilled in the art. Such coatings include cellulose acetate phthalate, polyvinyl acetate phthalate, shellac, styrene maleic acid copolymers, methacrylic acid copolymers and hydroxypropyl methylcellulose phthalate.

When the pharmaceutical compositions of the invention are enterically coated they are particularly useful for treating diseases of the lower gastrointestinal tract such as irritable bowel syndrome.

Thus when the pharmaceutical compositions of the invention contain the compounds described in EP-A-0501322 as active ingredient, e.g. [1-[2-[(methylsulphonyl)amino]ethyl]-4-piperidinyl]methyl 5-fluoro-2-methoxy-1H-indole- 3-carboxylate and pharmaceutically acceptable salts and solvates thereof, they are preferably enterically coated.

When the pharmaceutical compositions of the invention contain an $H_2$-antagonist or sumatriptan, they will not have an enteric coating.

When the inner layer or layers dissolves/erodes gradually it may comprise, in addition to the active ingredient, a pH independent hydrophilic polymer together with one or more fillers, as defined above, and also further excipients such as lubricants, disintegrants, surfactants, ionic salts as defined hereinbefore.

The concentration of active ingredient in the inner or outer layers or outer coating depends on the active ingredient employed and is conveniently from 30 to 100% w/w, with respect to the other excipients in the layer. Thus, for example, in the case of sumatriptan, a suitable concentration is 50% w/w (as succinate) and, for ranitidine, a suitable concentration is 95% w/w (as hydrochloride).

The weight ratio of inner layer or layers to outer polymer layer is conveniently in the range of 1:1 to 1:5, for example 1:1.3 to 1:4.3. The weight ratio of inner layer or layers to outer rapidly disintegrating coating (when present) is conveniently 1:1.

Where pulsed release dosage forms are provided the active ingredient is contained within a rapidly disintegrating inner layer.

It is a further advantage of the invention that pharmaceutical compositions (e.g. pulsed release compositions) are produced having a predictable and uniform release profile (i.e. the time-to-pulse is predictable and does not vary between individual dosage forms). For a fixed composition of outer layer and inner layer according to the invention, the release profile of the preparation will depend upon the thickness of the outer hydrophilic polymer coating. Thus if pharmaceutical compositions are to be produced having a uniform release profile, it is important that:
i) the coating thickness on each individual preparation should be uniform and effectively constant as between individual preparations; and
ii) the weight of polymer coat on each preparation should be effectively constant as between individual preparations.

The pharmaceutical compositions of the invention can be conveniently coated with an accurately known weight of polymer using conventional tabletting methods.

Thus in a further or alternative aspect the present invention provides a plurality of pharmaceutical preparations wherein the maximum variation in weight of the outer polymer layer does not exceed ±5% (e.g. ±2%) of the mean weight of the outer polymer layer.

In a further or alternative aspect the present invention also provides a plurality of pharmaceutical preparations wherein the maximum variation in thickness of the outer polymer layer does not exceed ±5% (e.g. ±2%) of the mean thickness of the outer polymer layer.

A plurality of pharmaceutical preparations means a production run of such preparations, or a course prescribed by a medical practitioner, or a bottle, container, packet or batch of such preparations.

Using conventional tabletting methods pharmaceutical compositions of the invention may conveniently be provided such that the outer polymer layer of each individual pharmaceutical preparation can be evenly distributed over the surface of that preparation.

Thus the invention further provides a pharmaceutical composition wherein the difference in thickness between the thinnest part of the outer layer and the thickest part of the outer layer is no more than 5% (e.g. 2%) of the mean outer layer thickness.

It should be appreciated that predictable and uniform release profiles may be obtained even when the outer polymer layer of the pharmaceutical preparation is not evenly distributed over the surface of the preparation, for example the core of the device may be off-set from the centre, in which case the time-to-pulse will depend upon the thickness of the outer polymer layer at its thinnest point.

Thus the invention further provides plurality of pharmaceutical compositions wherein the maximum variation in thickness of the thinnest part of the outer layer does not exceed ±5% (e.g. ±2%) of the mean thickness of the thinnest part of the outer layer.

In a further or alternative aspect the invention provides a plurality of pulsed-release dosage forms wherein the maximum variation in time-to-pulse does not exceed ±5% (e.g. ±2%) of the mean time-to-pulse.

In a preferred aspect the pulse release pharmaceutical compositions according to the invention provide a distinct pulse i.e. the release of active ingredient from the core after the initial predetermined time delay occurs over a relatively short time period (i.e. less than 30 minutes, e.g. less than 10 minutes) and there is no premature leakage of the active ingredient from the core.

The pharmaceutical compositions according to the invention may be adapted to provide a variety of unit doses depending on the active ingredient, the route of administration and the age and condition of the patient. Suitable doses will be readily appreciated by those skilled in the art.

Thus, in the case of sumatriptan, a suitable unit dose is 0.1 mg to 100 mg, e.g. 2 mg to 40 mg of the active ingredient per unit dose, e.g. 50 mg of sumatriptan as its succinate. Such unit doses may be administered one to four times a day, preferably twice a day.

When the pharmaceutical compositions according to the invention contain ranitidine, a convenient unit dose of ranitidine is 50-800 mg, preferably 75-600 mg, e.g. 150 mg, expressed as the weight of the free base. Such unit doses may be administered one to four times a day, preferably twice a day.

When the pharmaceutical compositions according to the invention contain cimetidine, a convenient unit dose of cimetidine is 200 mg or 400 mg expressed as the weight of free base.

When the pharmaceutical compositions according to the invention contain a compound described in a EP-A-0501322 convenient unit dose of the active ingredient is 1 mg to 100 mg expressed as the weight of free base, which may be administered, for example, 1 to 4 times per day.

The pharmaceutical compositions of the invention may be designed to deliver multiple unit doses, for example the pulsed release pharmaceutical compositions of the invention may provide an immediate dose of active ingredient followed by a subsequent dose after a predetermined time delay, thus the frequency of administration of medication is reduced.

The time-to-pulse will depend upon the active ingredient employed and the conditions being treated.

Thus, in the case of sumatriptan the pharmaceutical compositions of the invention conveniently provide an immediate dose of sumatriptan followed by a further dose after a time-delay of 1 to 6 hours (e.g. 1 to 3.5 hours). Alternatively, a pulsed release sumatriptan dosage form may be taken simultaneously with a conventional sumatriptan tablet to achieve the same immediate/delayed-release profile.

Sumatriptan pulsed-release compositions of the invention are of particular use in the treatment of patients suffering from predictable nocturnal cluster headaches where the patient can be administered with pulsed release dosage forms which deliver a dose of sumatriptan at an appropriate time during the night, for example 6 hours after administration.

When the pharmaceutical compositions according to the invention contain ranitidine, they may be designed to deliver a suitable unit dose (e.g. 150 mg) of ranitidine, for example immediately, followed by a subsequent suitable unit dose of ranitidine (e.g. a further dose of 150 mg) after a predetermined time delay (e.g. 2 to 5 hours).

When, the pharmaceutical compositions according to the invention contain cimetidine, they may provide an immediate dose of cimetidine (e.g. 200 or 400 mg) followed by a further dose of cimetidine (e.g. 200 or 400 mg) after a predetermined time delay.

The $H_2$-antagonist-containing pharmaceutical compositions according to the invention are of particular benefit in the treatment of reflux oesophagitis or diseases resulting in a very high gastric acid secretion e.g. Zollinger-Ellison syndrome.

When the pharmaceutical compositions according to the invention contain agents for treating lower gastrointestinal tract diseases, for example the compounds described in EP-A-0501322 in particular [1-[2-[(methylsulphonyl)amino]ethyl]-4-piperidinyl]methyl 5-fluoro-2-methoxy-1H-indole-3-carboxylate and pharmaceutically acceptable salts and solvates thereof, they may be designed to deliver a suitable unit dose after a predetermined time delay of, for example, 6 to 8 hours when the device has been enterically coated, or 4 to 6 hours when the device has not been enterically coated.

In designing dosage forms according to the invention in order to tailor the rate and manner of release of the active ingredients, certain factors are important and such factors include;

1. Polymer hydration rates. A pH independent polymer will conveniently be selected which will wet rapidly to form a gel layer, fast enough to protect the interior of the dosage form from either dissolving or disintegrating. If the polymer is too slow to hydrate, fluids may penetrate to the core, resulting in premature release of the drug. Another result of inadequate polymer hydration speed can be accelerated dissolving of the water soluble excipients in the polymer layer resulting in premature disintegration of the dosage form.

Polymer hydration rates can be manipulated by altering the methoxyl and hydroxypropyl ratios of the polymer.

For example, among the family of hydroxypropyl methylcelluloses, there are significant differences in the rate at which polymers will hydrate. This is due to varying proportions of the two chemical substituents attached to the cellulose backbone of HPMC, the hydroxypropyl and methoxyl substitution. The methoxy substituent is a relatively hydrophobic component and does not contribute as greatly to the hydrophilic nature of the polymer and the rate at which it will hydrate. The hydroxypropyl group however, does contribute greatly to the rate of polymer hydration. Thus by altering the methoxyl and hydroxypropyl ratio of the polymer, the polymer hydration rates can be altered.

2. Particle size. The particle size of the polymer can greatly influence the rate of polymer hydration. In general it will be preferable to use pH independent polymers (e.g. hydroxypropyl methylcellulose) of small particle size to ensure rapid polymer hydration. The particle size of the polymer will also allow some control over the compression characteristics of the dosage form.

The particle size of the filler(s) or any additional excipients in the polymer layer may also have a significant impact on release characteristics. In general, a fine particle size for insoluble fillers will be preferred and will contribute to a more uniform erosion of the polymer layer.

3. Polymer solution viscosity. The rate at which the surface gel layer penetrates the interior of the dosage form is governed to some extent by the viscosity of the gel as well as its erosion. Release of the active ingredient can be controlled by selecting pH independent hydrophilic polymers with different chain lengths and differing viscosities. Higher viscosity polymers result in more delayed release of the active ingredient. Polymers having a normal viscosity of around 100 cps at 2% concentration in water are preferred.

4. Polymer concentration. Increasing the concentration of the pH independent hydrophilic polymer relative to the other constituents of the outer layer increases the viscosity of the gel that forms on the surface of the dosage form. Therefore, an increase in the level of polymer used will generally lead to a greater delay in release of the active ingredient.

An increase in the concentration of polymer also tends to decrease the sensitivity of the formulation to changes in particle size or hydration rates of polymers.

5. Presence of soluble/insoluble and swelling/non-swelling fillers. Soluble fillers in the polymer layer may affect gel viscosity on the surface of the dosage form. The soluble materials will compete with the polymer for the available water.

Release of insoluble fillers occurs through an erosion mechanism. As the polymer dissolves away exposing new layers, the insoluble filler will be released. Preferably the combination of swelling and non-swelling fillers in the outer polymer layer will be controlled to avoid stress fractures occurring in the polymer layer leading to premature disintegration of the core. Generally, the insoluble fillers should be used at relatively low concentrations, for example less than 15% by weight of the dosage form.

Conveniently an insoluble but swelling filler, such as microcrystalline cellulose, is used so that release characteristics are modified due to a change in the rate of swelling, but no stress fractures occur.

6. Presence of surfactants and ionic salts. When ionic salts are used in the formulation of the polymer layer they can compete with the polymer for the available water altering the rate of polymer hydration.

Inclusion of surfactants such as anionic surfactants, for example sodium lauryl sulphate, can give rise to higher viscosities and slower release that might otherwise be expected.

7. Thickness of the outer polymer layer. As the thickness of the outer polymer layer is increased, the delay time for release of the active ingredient in the inner core increases. Modification of the surface to volume ratio of the dosage form may also substantially alter the release characteristics.

The pharmaceutical compositions according to the invention may be prepared according to conventional methods known in the art using conventional tabletting machinery.

Thus, for example, the pH independent hydrophilic polymer may be blended with one or more fillers, and optionally other excipients, and compressed onto a core of one or more inner layers each comprising an active ingredient.

Cores of active substance may be prepared, for example, by compression of material produced by dry slugging, wet granulation or dry blending.

Blends for rapidly disintegrating outer coatings may be prepared in the same way and compressed onto the pH independent hydrophilic polymer coated cores.

The invention is further illustrated by the following examples, which are non-limiting. The following examples relate specifically to tablets for oral administration, however by altering the shape of the dosage forms, suppositories and pessaries suitable for rectal and vaginal administration may be obtained using the same core and coating compositions.

EXAMPLE 1

Tablet for pulsed release

| Tablet Core | % w/w |
| --- | --- |
| Sufotidine | 20 |
| Microcrystalline Cellulose | 59 |
| Pregelatinized Starch | 15 |
| Polyvinylpyrrolidone | 5 |
| Sodium Stearyl Fumerate | 1 |

Sufotidine was dry mixed with microcrystalline cellulose, pregelatinized starch and polyvinylpyrrolidone and the mixture granulated using isopropyl alcohol as the granulation fluid. The granulate was air dried, sieved and blended with sodium stearyl fumerate before compression on a suitable tablet press to produce 50 mg core tablets containing 10 mg of sufotidine which were 4.76 mm in diameter and 3.0 mm in thickness.

| Outer layer | % w/w |
| --- | --- |
| Hydroxypropyl Methylcellulose* | 35 |
| Microcrystalline Cellulose | 40 |
| Dibasic Calcium Phosphate | 23 |
| Colloidal Silicon Dioxide | 1 |
| Sodium Stearyl Fumerate | 1 |

*normal viscosity 2% in water = 100 cps

The excipients were dry mixed and the core tablet compression coated using the resulting blend to produce 265 mg tablets, 8.7 mm in diameter and 4.0 mm in thickness.

The release of the drug from the tablets was monitored using a dissolution tester which conforms to the requirements of the USP, in which 500 ml of distilled water or simulated gastric fluid or simulated intestinal fluid was maintained at 37° C. and used as the dissolution medium. The USP 1 dissolution method was used at a rotation speed of 250 rpm.

Pulsatile release of sufotidine is obtained after a period of about 3.5 hours in each of the dissolution media.

In the following examples numbered 2 to 9 the dimensions of the tablet cores and polymer coat are identical to those in Example 1.

EXAMPLE 2

Tablet for Pulsed release

| | % w/w |
| --- | --- |
| Tablet Core | |
| Sufotidine | 20 |
| Microcrystalline Cellulose | 59 |
| Pregelatinized Starch | 15 |
| Polyvinylpyrrolidone | 5 |

| | % w/w |
| --- | --- |
| Sodium Stearyl Fumerate | 1 |
| Outer layer | |
| Hydroxypropyl Methylcellulose* | 77 |
| Microcrystalline Cellulose | 12 |
| Dibasic Calcium Phosphate | 9 |
| Colloidal Silicon Dioxide | 1 |
| Sodium Stearyl Fumerate | 1 |

*normal viscosity 2% in water = 100 cps

Pulsed release tablets were prepared and tested as for Example 1.

Pulsatile release of the active ingredient was obtained after a period of about 9.2 hours in simulated intestinal fluid and about 6.2 hours in distilled water or simulated gastric fluid.

EXAMPLE 3

Tablet for delayed sustained release

| Outer layer | % w/w |
| --- | --- |
| Hydroxypropyl Methylcellulose* | 35 |
| Microcrystalline Cellulose | 40 |
| Dibasic Calcium Phosphate | 23 |
| Colloidal Silicon Dioxide | 1 |
| Sodium Stearyl Fumerate | 1 |

*normal viscosity 2% in water = 4000 cps

Tablets cores prepared according to Example 1 were compression coated as described in Example 1 and tested as described therein.

Sustained release of the active ingredient was obtained after a delay period of 3 hours in simulated gastric fluid.

EXAMPLE 4

Tablet for pulsed release

| Tablet core | % w/w |
| --- | --- |
| Salbutamol Sulphate | 19.28 |
| Microcrystalline Cellulose | 64.72 |
| Pregelatinized Starch | 15.00 |
| Sodium Stearyl Fumerate | 1.00 |

Salbutamol sulphate was mixed with the excipients and the mixture compressed on a suitable tablet press to produce tablet cores of containing 8 mg of salbutamol base.

| Outer layer | % w/w |
| --- | --- |
| Hydroxypropyl Methylcellulose* | 30 |
| Microcrystalline Cellulose | 43 |
| Dibasic Calcium Phosphate | 25 |
| Colloidal Silicon Dioxide | 1 |
| Sodium Stearyl Fumerate | 1 |

*normal viscosity 2% in water = 100 cps

Pulsed release of salbutamol is obtained after a period of about 3 hours in each of the dissolution media.

EXAMPLE 5

Tablet for sustained release of a first active and delayed sustained release of a second active A first active is dispersed throughout a polymer matrix comprising hydroxypropyl methylcellulose (normal viscosity 2% in water=100 cps) (30% w/w), microcrystalline cellulose (43% w/w), dibasic calcium phosphate (25% w/w), colloidal silicon dioxide (1% w/w) and sodium stearyl fumerate (1% w/w). The blend is used to compression coat a core tablet, prepared as described in Example 1, containing a second active.

Sustained release of the first active and delayed sustained release of the second active is obtained.

EXAMPLE 6

Tablet for pulsed release of a first active and sustained release of a second active A first active is dispersed throughout a polymer matrix comprising hydroxypropyl methylcellulose (normal viscosity 2% in water=100 cps) (70% w/w), microcrystalline cellulose (17% w/w), and dibasic calcium phosphate (13% w/w).

A second active is dispersed throughout an excipient base comprising hydroxypropyl methylcellulose (normal viscosity 2% in water=100 cps) (77% w/w), microcrystalline cellulose (12% w/w), dibasic calcium phosphate (9% w/w), colloidal silicon dioxide (1% w/w) and sodium stearyl fumerate (1% w/w). This mix is compressed and the resulting tablets are further compression coated with the polymer matrix containing the first active.

Pulsed release of the first active and sustained release of the second active is obtained.

EXAMPLE 7

Tablet for controlled release of three actives

A device is manufactured which contains a core tablet which is compression coated with an intermediate layer and finally coated with an outer layer.

The core tablet is manufactured as described in Example 1, this tablet is first compression coated with the excipient base, followed by further coating with the polymer matrix layer as outlined in Example 6.

Immediate release of the drug, followed by sustained release and finally pulsed release is obtained.

By choosing an appropriate blend of excipients, the core tablet can also be formulated so that instead of the core disintegrating, it swells, resulting in sustained release of the final active instead of pulse release.

EXAMPLE 8

Sufotidine core tablets (manufactured as in Example 1) were compression coated using a blend composed of 74.4% w/w HPMC (nominal viscosity, 2% in water=100 cps), 11.6% w/w microcrystalline cellulose, 8.2% w/w dibasic calcium phosphate, 3.3% w/w piroxicam, 0.97% w/w colloidal silicon dioxide and 0.97% w/w sodium stearyl fumerate.

The release of the drug from the tablets was monitored using a dissolution tester which conforms to the requirements of the USP, in which 500ml of simulated gastric fluid was maintained at 37° and used as the dissolution medium. The USP1 dissolution method was used at a rotation speed of 250 rpm.

Sustained release of piroxicam and pulsed release of sufotidine was obtained.

EXAMPLE 9

Sufotidine pulse release tablets were prepared as described in Example 1. These tablets were given an enteric coating by spraying onto the tablets a solution containing methacrylic acid copolymer and triacetin (90:10) in isopropyl alcohol. This enteric coat is insoluble below pH6.0 and also in natural and simulated gastric fluid. The coat, however, is soluble in the region of the digestive tract where the pH is above 7.0.

The release of the drug from the tablets was monitored in vitro using a dissolution tester which conforms to the requirements of the USP, in which either simulated gastric fluid (pH1.2) or intestinal fluid (pH7.2) were maintained at 37°. The USP1 dissolution method was used at a rotation speed of 250 rpm.

When tested in simulated gastric fluid (pH1.2) release of drug from the device was prevented throughout the period of testing (6.5 hours). When transferred to simulated intestinal fluid (pH 7.2) however, a pulsed release of sufotidine was achieved after 4.5 hours.

EXAMPLE 10

Tablet for immediate release and pulsed release

| Tablet Core | % w/w |
| --- | --- |
| Sumatriptan (as succinate) | 50 |
| Microcrystalline cellulose | 23 |
| Lactose | 23 |
| Polyvinylpyrrolidone | 2 |
| Sodium stearyl fumerate | 2 |
| * Isopropyl Alcohol | qs |

* not present in the final product.

Sumatriptan was dry mixed with microcrystalline cellulose and lactose and the mixture was granulated using a granulating fluid composed of polyvinylpyrrolidone dissolved in isopropyl alcohol. The granulate was dried in a fluid bed drier, sieved and blended with sodium stearyl fumerate before compression on a suitable tablet press to produce 100 mg core tablets containing 50 mg of sumatriptan (as succinate) which were 5.5 mm in diameter and 3.0 mm in thickness.

| Intermediate Polymer Layer | % w/w |
| --- | --- |
| * Hydroxypropyl Methylcellulose | 35 |
| Microcrystalline Cellulose | 40 |
| Dibasic calcium phosphate | 23 |
| Colloidal silicon dioxide | 1 |
| Sodium stearyl fumerate | 1 |

* normal viscosity 2% in water = 100 cps.

The excipients for the intermediate layer were dry mixed and the core tablet was compression coated using the resulting blend to produce 230 mg tablets, 8.7 mm in diameter and 4.0 mm in thickness.

Outer Sumatriptan Layer

Same formulation as the core tablet.

The compression coated tablets were further coated with 100 mg of the tablet core blend by compression.

The release of the drug was monitored using dissolution equipment which conforms to the requirements of the USP, in which 900 ml of simulated gastric fluid was maintained at 37° C. and used as the dissolution medium. The USP 1 dissolution method was used at a rotation speed of 250 rpm.

Initial immediate release of sumatriptan was obtained followed by pulsatile release of the drug after a period of about 1.5 hours.

The core tablets described above were also coated with the above intermediate polymer blend to give tablets of 11.0 mm in diameter which were further coated with the outer sumatriptan layer blend (100 mg). The resulting tablets (720 mg) gave initial immediate release of sumatriptan followed by pulsatile release of the drug after a period of 3 hours.

EXAMPLE 11

Tablet for pulsed release

| Tablet Core | % w/w |
| --- | --- |
| Sumatriptan (as succinate) | 50 |
| Microcrystalline cellulose | 23 |
| Lactose | 23 |
| Polyvinylpyrrolidone | 2 |
| Sodium stearyl fumerate | 2 |
| * Isopropyl Alcohol | qs |

* not present in the final product.

Sumatriptan was dry mixed with microcrystalline cellulose and lactose and the mixture was granulated using a granulating fluid composed of polyvinylpyrrolidone dissolved in isopropyl alcohol. The granulate was dried in a fluid bed drier, sieved and blended with sodium stearyl fumerate before compression on a suitable tablet press to produce 100 mg core tablets containing 50 mg of sumatriptan (as succinate) which were 5.5 mm in diameter and 3.0 mm in thickness.

| Polymer Layer | % w/w |
| --- | --- |
| * Hydroxypropyl Methylcellulose | 35 |
| Microcrystalline Cellulose | 40 |
| Dibasic calcium phosphate | 23 |
| Colloidal silicon dioxide | 1 |
| Sodium stearyl fumerate | 1 |

* normal viscosity 2% in water = 100 cps.

The excipients for the polymer layer were dry mixed and the core tablet was compression coated using the resulting blend to produce 340 mg tablets, 9.0 mm in diameter and 4.1 mm in thickness.

The release of the drug was monitored using dissolution equipment which conforms to the requirements of the USP in which either, distilled water, simulated intestinal fluid or simulated gastric fluid was maintained at 37° C. and used as the dissolution medium. The USP 1 dissolution method was used at a rotation speed of 250 rpm.

Pulsatile release of sumatriptan was obtained after a period of about 2.5 hours in each of the dissolution media.

The core tablets described above were also coated with the above polymer blend to give 460 mg tablets, 11 mm in diameter and 4.5 mm in thickness.

Pulsatile release of sumatriptan was obtained after a period of 3.5 hours in each of the above media.

EXAMPLE 12

Tablet for pulsed release

| Tablet Core | % w/w |
| --- | --- |
| Ranitidine hydrochloride | 95 |
| Polyvinylpyrrolidone | 4 |
| Magnesium Stearate | 1 |
| * Isopropyl Alcohol | qs |

* not present in the final product

The ranitidine hydrochloride was granulated using a granulating fluid composed of polyvinylpyrrolidone dissolved in isopropyl alcohol. The granulate was dried in a fluid bed drier, sieved and blended with magnesium stearate before compression on a suitable tablet press to produce 177 mg core tablets containing 150 mg of ranitidine (as base) which were 7.5 mm in diameter and 4.5 mm in thickness.

| Outer Layer | % w/w |
| --- | --- |
| * Hydroxypropyl Methylcellulose | 23.0 |
| Microcrystalline Cellulose | 40.6 |
| Dibasic calcium phosphate | 35.0 |
| Colloidal silicon dioxide | 0.7 |
| Sodium stearyl fumerate | 0.7 |

* normal viscosity 2% in water = 100 cps.

The excipients of the outer layer were dry mixed and the core tablet was compression coated using the resulting blend to produce 730 mg tablets, 12 mm in diameter and 5.6 mm in thickness.

The release of the drug was monitored using dissolution equipment which conforms to the requirements of the USP, in which 900 ml of simulated gastric fluid was maintained at 37° C. and used as the dissolution medium. The USP 1 dissolution method was used at a rotation speed of 250 rpm. A pulsatile release of drug was obtained after a period of about 3 hours.

EXAMPLE 13

Tablet for immediate release and pulsed release

Pulse delivery devices containing ranitidine were manufactured as described in Example 1.

The compression coated tablets were further coated with 177 mg of the tablet core blend by compression on a suitable tablet press.

The release of the drug was monitored using dissolution equipment which conforms to the requirements of the USP in which 900 ml of simulated gastric fluid was maintained at 37° C. and used as the dissolution medium. The USP 1 dissolution method was used at a rotation speed of 250 rpm.

Initial immediate release of ranitidine was obtained followed by pulsatile release of the drug after a period of about 3 hours.

EXAMPLE 14

Tablet for pulsed release

| Tablet Core | % w/w |
| --- | --- |
| Ranitidine hydrochloride | 95 |
| Polyvinylpyrrolidone | 4.5 |
| Magnesium Stearate | 0.5 |
| * Isopropyl Alcohol | qs |

* not present in the final product

The ranitidine hydrochloride was granulated using a granulating fluid composed of polyvinylpyrrolidone dissolved in isopropyl alcohol. The granulate was dried in a fluid bed drier, sieved and blended with magnesium stearate before compression on a suitable tablet press to produce 177 mg core tablets containing 150 mg of ranitidine (as base) which were 9.0 mm in diameter and 3.4 mm in thickness.

| Outer Layer | % w/w |
| --- | --- |
| * Hydroxypropyl Methylcellulose | 35.0 |
| Microcrystalline Cellulose | 40.0 |
| Dibasic calcium phosphate | 23.0 |
| Colloidal silicon dioxide | 1.0 |
| Sodium stearyl fumerate | 1.0 |

* normal viscosity 2% in water = 100 cps.

The excipients of the outer layer were dry mixed and the core tablet was compression coated using the resulting blend to produce 530 mg tablets, 12 mm in diameter and 5.1 mm in thickness.

The release of the drug was monitored using dissolution equipment which conforms to the requirements of the USP, in which 900 ml of simulated gastric fluid was maintained at 37° C. and used as the dissolution medium. The USP 1 dissolution method was used at a rotation speed of 250 rpm. A pulsatile release of drug was obtained after a period of about 2 hours.

EXAMPLE 15

Tablet for pulsed release

| Tablet Core | % w/w |
|---|---|
| Ranitidine hydrochloride | 95 |
| Polyvinylpyrrolidone | 4.5 |
| Magnesium Stearate | 0.5 |
| * Isopropyl Alcohol | qs |

* not present in the final product

The ranitidine hydrochloride was granulated using a granulating fluid composed of polyvinylpyrrolidone dissolved in isopropyl alcohol. The granulate was dried in a fluid bed drier, sieved and blended with magnesium stearate before compression on a suitable tablet press to produce 177 mg core tablets containing 150 mg of ranitidine (as base) which were 7.5 mm in diameter and 4.5 mm in thickness.

| Outer Layer | % w/w |
|---|---|
| * Hydroxypropyl Methylcellulose | 33.3 |
| Microcrystalline Cellulose | 38.1 |
| Dibasic calcium phosphate | 26.7 |
| Colloidal silicon dioxide | 0.95 |
| Sodium stearyl fumerate | 0.95 |

* normal viscosity 2% in water = 100 cps.

The excipients of the outer layer were dry mixed and the core tablet was compression coated using the resulting blend to produce 530 mg tablets, 12 mm in diameter and 5.1 mm in thickness.

The release of the drug was monitored using dissolution equipment which conforms to the requirements of the USP, in which 900 ml of simulated gastric fluid was maintained at 37° C. and used as the dissolution medium. The USP 1 dissolution method was used at a rotation speed of 250 rpm. A pulsatile release of drug was obtained after a period of about 3 hours.

We claim:

1. A pharmaceutical composition comprising:
   (a) an outer layer comprising a pH independent hydrophilic polymer together with one or more fillers; and
   (b) one or more inner layers each comprising an active ingredient which is an H2-antagonist, a serotonin agonist or a serotonin antagonist;
   wherein the outer layer is gradually removed by a combination of dissolution and erosion following administration and the inner layer or layers disintegrates rapidly in less than 30 minutes, once exposed.

2. A pharmaceutical composition comprising:
   (a) an outer layer comprising a pH independent hydrophilic polymer together with one or more fillers; and
   (b) one or more layers each comprising an active ingredient selected from sumatriptan or a pharmaceutically acceptable salt thereof or [1 -[2[(methylsulphonyl)amino]ethyl]-4-piperidinyl]methyl-5-fluoro-2-methoxy-1H-indole-3-carboxylate; ondansetron; 2,3,4,5-tetrahydro-5-methyl-2-[(5-methyl-1H-imidazol-4-yl)methyl]-1H-pyridol[4,3-b]indol- 1-one;(+)-1,2,3,9-tetrahydro-9-methyl-3[(5-methyl-1H-imidazol-4-yl)methyl]-4H-carbazol-4-one; 6-fluoro-2,3,4,5-tetrahydro-5-methyl-2-[(5-methyl-1H-imidazol-4-yl)-methyl]-1H-pyrido[4,3-b]indol-1-one; or a pharmaceutically acceptable salt or solvate thereof;
   wherein the outer layer is gradually removed by a combination of dissolution and erosion following administration and the inner layer or layers is gradually removed by a combination of dissolution and erosion or disintegrates rapidly once exposed.

3. A pharmaceutical composition as claimed in claim 1 having a single inner core layer comprising an active ingredient.

4. A pharmaceutical composition as claimed in claim 1 having an additional rapidly disintegrating outer coating, surrounding the pH independent hydrophilic polymer layer, comprising an active ingredient.

5. A pharmaceutical composition as claimed in claim 2 wherein the outer layer comprises hydroxypropylmethylcellulose and a filler which is microcrystalline cellulose, dibasic calcium phosphate or a mixture thereof.

6. A pharmaceutical composition as-claimed in claim 1 wherein the H2-antagonist is ranitidine or a pharmaceutically acceptable salt thereof.

7. A pharmaceutical composition as claimed in claim 1 wherein the outer layer comprises hydroxypropylmethylcellulose and a filler which is microcrystalline cellulose, dibasic calcium phosphate, or a mixture thereof.

8. A pharmaceutical composition as claimed in claim 1 wherein the pH independent hydrophilic polymer has a normal viscosity of 100 cps at 2% concentration in water.

9. A pharmaceutical composition as claimed in claim 1 wherein the pH independent hydrophilic polymer is a cellulose ether; polyvinylpyrrolidone; a mixture of natural hydrophilic gums; or mixtures thereof.

10. A pharmaceutical composition as claimed in claim 1 wherein the cellulose ether is hydroxypropylmethylcellulose.

11. A pharmaceutical composition as claimed in claim 1 wherein the outer layer additionally comprises a lubricant and a glidant.

12. A process for the preparation of a pharmaceutical composition as claimed in claim 1 wherein an outer layer blend comprising a pH independent hydrophilic polymer together with one or more fillers is compression coated onto a core of one or more inner layers each comprising an active ingredient.

13. A process as claimed in claim 12 wherein the pharmaceutical composition is further compression coated with a blend comprising an active ingredient.

14. A pharmaceutical composition as claimed in claim 1, wherein the rapid disintegration takes place in less than 10 minutes.

15. A pharmaceutical composition as claimed in claim 1 wherein the serotonin agonist is sumatriptan or a pharmaceutically acceptable salt thereof, and the serotonin antagonist is [1-[2-[(methylsulphonyl)amino]ethyl]-4-piperidinyl]methyl-5-fluoro-2-methoxy-1H-indole-3-carboxylate; ondansetron; 2,3,4,5-tetrahydro-5-methy 1-2-[(5-methyl-1H-imidazol-4-yl)methyl]-1H-pyrido[4,3-b]indol-1-one;(±)-1,2,3,9-tetrahydro-9-methyl-3-[(5-methyl-1H-imidazol-4-yl)methyl]-4H-carbazol-4-one;6-fluoro-2,3,4,5-tetrahydro-5-methyl-2-[(5-methyl-1H-imidazol-4-yl)methyl]-1H-pyrido[4,3-b]indol-1-one; or a pharmaceutically acceptable salt of solvate thereof.

* * * * *